(12) United States Patent
Eura et al.

(10) Patent No.: US 10,094,779 B2
(45) Date of Patent: Oct. 9, 2018

(54) OPTICAL MEASUREMENT DEVICE AND OPTICAL MEASUREMENT METHOD

(71) Applicant: HAMAMATSU PHOTONICS K.K., Hamamatsu-shi, Shizuoka (JP)

(72) Inventors: Shigeru Eura, Hamamatsu (JP); Kengo Suzuki, Hamamatsu (JP); Kenichiro Ikemura, Hamamatsu (JP); Kazuya Iguchi, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 135 days.

(21) Appl. No.: 15/312,771

(22) PCT Filed: Apr. 7, 2015

(86) PCT No.: PCT/JP2015/060876
§ 371 (c)(1),
(2) Date: Nov. 21, 2016

(87) PCT Pub. No.: WO2015/178113
PCT Pub. Date: Nov. 26, 2015

(65) Prior Publication Data
US 2017/0212047 A1    Jul. 27, 2017

(30) Foreign Application Priority Data
May 23, 2014 (JP) ................................ 2014-106816

(51) Int. Cl.
*G01N 21/64* (2006.01)
*G01J 3/443* (2006.01)
*G01J 3/02* (2006.01)

(52) U.S. Cl.
CPC ............ *G01N 21/64* (2013.01); *G01J 3/0254* (2013.01); *G01J 3/443* (2013.01); *G01N 2201/12753* (2013.01)

(58) Field of Classification Search
CPC ........................................................ G01J 3/02
See application file for complete search history.

(56) References Cited

U.S. PATENT DOCUMENTS 4,583,860 A * 4/1986 Butner ................ G01N 21/255
                                                              250/228
7,339,665 B2 * 3/2008 Imura ....................... G01J 3/28
                                                              356/243.1
(Continued)

FOREIGN PATENT DOCUMENTS

CN        101932926        12/2010
CN        102192786         9/2011
(Continued)

OTHER PUBLICATIONS

International Preliminary Report on Patentability dated Dec. 8, 2016 for PCT/JP2015/060876.

(Continued)

*Primary Examiner* — Yara B Green
(74) *Attorney, Agent, or Firm* — Drinker Biddle & Reath LLP

(57) ABSTRACT

An optical measurement device inputs excitation light to an integrating sphere in which a sample is disposed, irradiates the sample with the excitation light having a predetermined beam cross-section, detects measurement light output from the integrating sphere by a photodetector, and acquires intensity data of the sample. The optical measurement device includes a storage unit in which correction data is stored and an optical characteristic calculation unit for calculating optical characteristics of the sample based on the intensity data of the sample and the correction data. The correction data is calculated based on first corrective intensity data and second corrective intensity data. The predetermined beam cross-section is covered with the first light (Continued)

absorbing member and covers the second light absorbing member.

20 Claims, 8 Drawing Sheets

(56) References Cited

U.S. PATENT DOCUMENTS

| | | | |
|---|---|---|---|
| 8,592,780 B2 * | 11/2013 | Iguchi | G01N 21/645 250/458.1 |
| 2011/0235035 A1 | 9/2011 | Iguchi et al. | |

FOREIGN PATENT DOCUMENTS

| | | |
|---|---|---|
| CN | 103344621 | 10/2013 |
| JP | H09-292281 A | 11/1997 |
| JP | 2003-215041 A | 7/2003 |
| JP | 2004-309323 | 11/2004 |
| JP | 2011-196735 A | 10/2011 |
| JP | 2014-149266 A | 8/2014 |
| WO | WO-2009/050536 A1 | 4/2009 |
| WO | WO-2010/084566 A1 | 7/2010 |

OTHER PUBLICATIONS

N. C. Greenham et al., "Measurement of absolute photoluminescence quantum efficiencies in conjugated polymers", Chemical Physics Letters, vol. 241, Jul. 14, 1995, p. 89-p. 96.

Y. Ichino, "Theoretical Analysis of Integrating Sphere-based Absolute Photoluminescence Quantum Efficiency Measurement", The 71st Japan Society of Applied Physics Meeting, 14p-NK-6, Sep. 12, 2010.

Y. Kawamura et al., "Simple Accurate System for Measuring Absolute Photoluminescence Quantum Efficiency in Organic Solid-State Thin Films", Japanese Journal of Applied Physics, Nov. 10, 2004, vol. 43, No. 11A, p. 7729-p. 7730.

J. de Mello et al., "An Improved Experimental Determination of External Photoluminescence Quantum Efficiency", Advanced Materials, 1997, vol. 9, No. 3, p. 230-p. 232.

Jan Valenta, "Determination of absolute quantum yields of luminescing nanomaterials over a broad spectral range: from the intergrating sphere theory to the correct methodology" Nanoscience Methods, vol. 3, No. 1, Jan. 10, 2014, p. 11-p. 27, XP055313394.

Christian Wurth et al., "Evaluation of a Commercial Integrating Sphere Setup for the Determination of Absolute Photoluminescence Quantum Yields of Dilute Dye Solutions", Applied Spectroscopy, vol. 64, No. 7, Jan. 1, 2010, p. 733-p. 741, XP055088622.

* cited by examiner

Fig.4
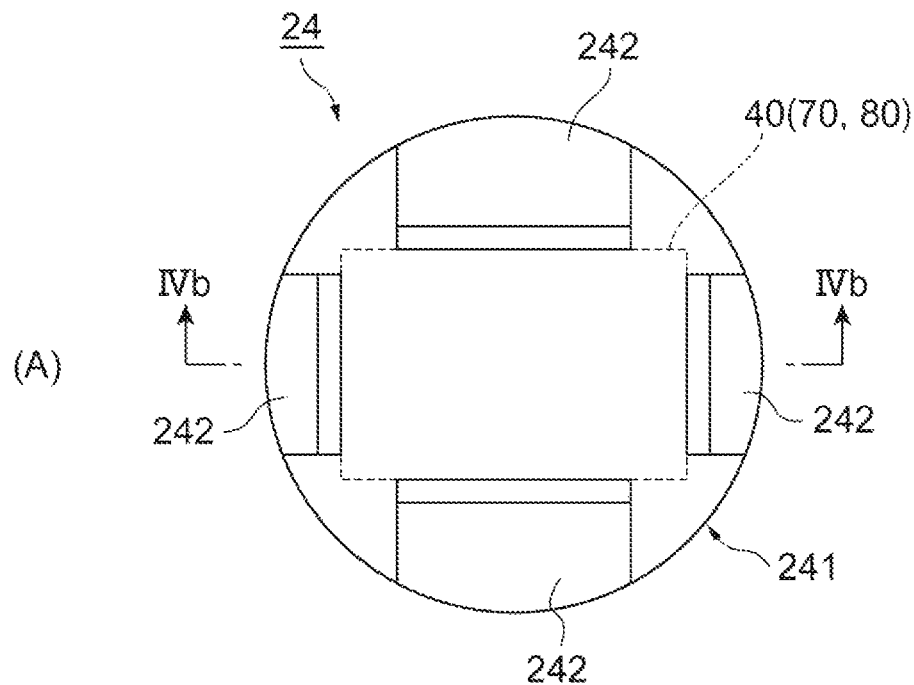
(A)
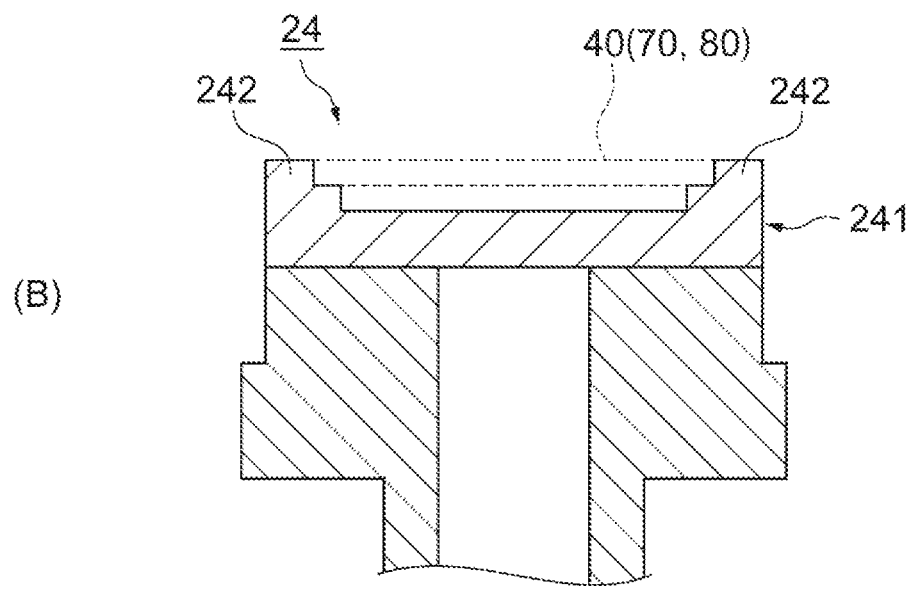
(B)

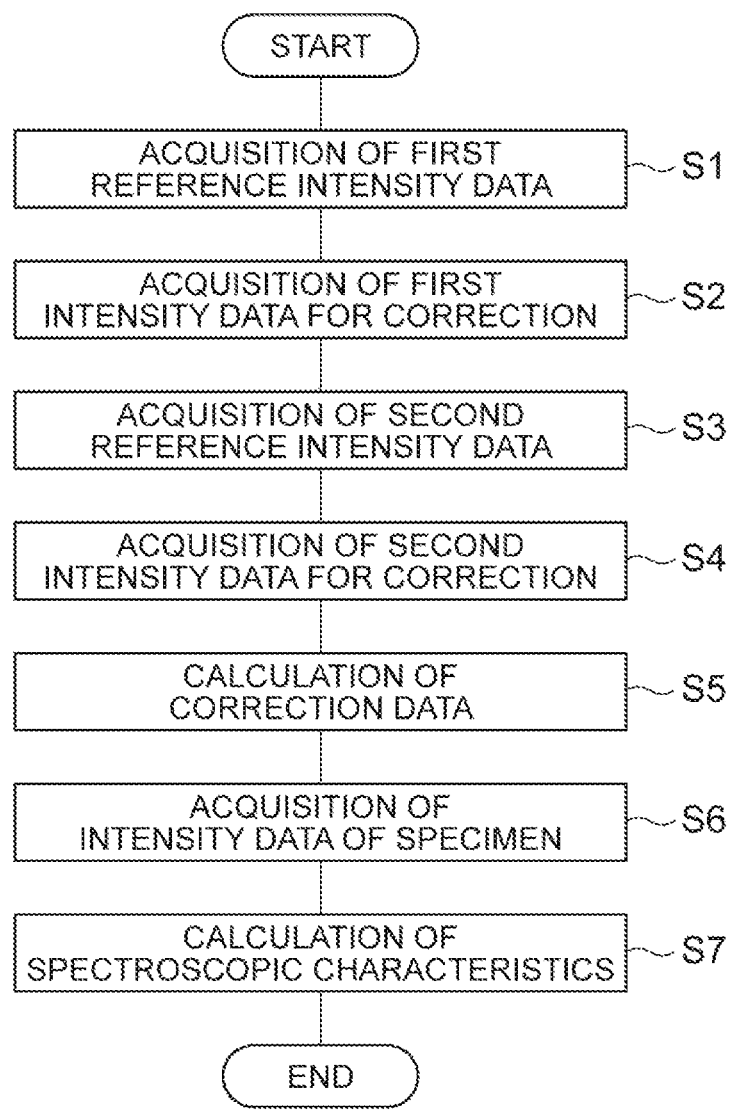

OPTICAL MEASUREMENT DEVICE AND OPTICAL MEASUREMENT METHOD

TECHNICAL FIELD

An aspect of the present invention relates to an optical measurement device and an optical measurement method.

BACKGROUND ART

An optical measurement device for irradiating a sample, which is an object to be measured, with excitation light and detecting measurement light has been known in the related art. As this kind of technique, for example, Patent Literature 1 discloses an absolute fluorescence quantum efficiency measurement device that obtains the absorptance of a sample from a measured value of a reflectance obtained using a spectroscopic reflectance standard in an integrating sphere and a measured value of a reflectance obtained using the sample when obtaining internal quantum efficiency (emission quantum yield).

For example, Patent Literature 2 discloses a quantum efficiency measurement device that measures excitation light absorbed in a sample in a state in which excitation light having passed through the sample is reflected in an integration space and measures light generated from the sample in a state in which the excitation light having passed through the sample is not reflected in the integration space. The quantum efficiency measurement device disclosed in Patent Literature 2 reduces a measurement error, which is caused by re-excitation (secondary excitation), by performing two-step measurement processing. Non Patent Literatures 1 to 3 disclose devices that irradiate a sample with excitation light having a predetermined beam cross-section so that the predetermined beam cross-section is surrounded by (covered with) the sample, and calculate internal quantum efficiency and external quantum efficiency internal quantum efficiency×absorptance) on the premise that the area of the sample at an irradiation position of the excitation light (hereinafter, simply referred to as "the area of the sample") is larger than the predetermined beam cross-section (beam diameter).

CITATION LIST

Patent Literature

Patent Literature 1: Japanese Unexamined Patent Publication No. H9-292281
Patent Literature 2: Japanese Unexamined Patent Publication No. 2003-215041

Non Patent Literature

Non Patent Literature 1: "Measurement of absolute photoluminescence quantum efficiencies in conjugated polymers Chemical Physics Letters Volume 241", Issues 1-2, 14 Jul. 1995, Pages 89-96, N. C. Greenham, I. D. W. Samuel, G. R. Hayes, R. T. Phillips, Y. A. R. R. Kessener, S. C. Moratti, A. B. Holmes, R. H. Friend
Non Patent Literature 2: "An improved experimental determination of external photoluminescence quantum efficiency Advanced Materials", Vol. 9, Issue 3, March 1997, Pages 230-232, John C. de Mello, H. Felix Wittmann, Richard H. Friend
Non Patent Literature 3: "Theoretical examination of a method of measuring absolute fluorescence quantum efficiency using an integrating sphere", 71st academic lecture of Japan Society of Applied Physics (Sep. 12, 2010), 14p-NK-6, ICHINO YOSHIAKI (2010.9.12) 14p-NK-6

SUMMARY OF INVENTION

Technical Problem

In the related arts, as described above, for the calculation of optical characteristics, such as an absorptance, internal quantum efficiency, and external quantum efficiency, a sample present in the light integrator is irradiated with the excitation light having the predetermined beam cross-section and the measurement light output from the light integrator is detected. Meanwhile, an absorptance is a parameter that is contrary to a reflectance, and has the same meaning as "1-reflectance".

However, according to a certain magnitude relationship between the area of the sample and the area of the predetermined beam cross-section of the excitation light (whether the predetermined beam cross-section is covered with the sample or covers the sample), there is a concern that optical characteristics to be calculated may be estimated so as to be different from true values. It is found that an absorptance and external quantum efficiency among the optical characteristics can be accurately obtained using an area ratio correction value relating to a ratio of the area of the predetermined beam cross-section and the area of the sample as represented in, for example, the following Equation (i), but there is a case in which it is difficult to measure the area of the beam cross-section of the excitation light in the light integrator.

$$H = (S_2/S_1) \times H' \quad (i)$$

H: optical characteristics having been corrected
H': optical characteristics not yet corrected
$S_1$: the area of the sample
$S_2$: the area of the predetermined beam cross-section of the excitation light An object of an aspect of the invention is to provide an optical measurement device and an optical measurement method that can accurately obtain optical characteristics even though not directly measuring the area of a beam cross-section of excitation light.

Solution to Problem

According to an aspect of the invention, there is provided an optical measurement device for irradiating a sample with excitation light and detecting measurement light. The optical measurement device includes a light integrator in which the sample is disposed, an optical system for inputting the excitation light to the light integrator and irradiating the sample with the excitation light having a predetermined beam cross-section, a photodetector for detecting measurement light output from the light integrator and outputting intensity data of the sample at one or a plurality of wavelengths, a storage unit in which correction data is stored, and an optical characteristic calculation unit for calculating optical characteristics of the sample based on the intensity data of the sample output from the photodetector and the correction data stored in the storage unit. The correction data is a correction value calculated based on first corrective intensity data, which is a detection value of first measurement light output from the light integrator when a first light absorbing member disposed in the light integrator is irradiated with the excitation light having the predetermined beam cross-section, and second corrective intensity data, which is a detection value of second measurement light output from the light integrator when a second light absorbing member disposed in the light integrator is irradiated with the excitation light having the predetermined beam cross-section. The predetermined beam cross-section of the excitation light is covered with the first light absorbing member and covers the second light absorbing member.

Further, according to another aspect of the invention, there is provided an optical measurement device for irradiating a sample with excitation light and detecting measurement light. The optical measurement device includes a light integrator in which the sample is disposed, an optical system for inputting the excitation light to the light integrator and irradiating the sample with the excitation light having a predetermined beam cross-section, a photodetector for detecting measurement light output from the light integrator and outputting intensity data of the sample at one or a plurality of wavelengths, a storage unit in which correction data is stored, and an optical characteristic calculation unit for calculating optical characteristics of the sample based on the intensity data of the sample output from the photodetector and the correction data stored in the storage unit. The correction data is a correction value calculated based on first corrective intensity data, which is a detection value of first measurement light output from the light integrator when a first light absorbing member disposed in the light integrator is irradiated with the excitation light having the predetermined beam cross-section, and second corrective intensity data, which is a detection value of second measurement light output from the light integrator when a second light absorbing member disposed in the light integrator is irradiated with the excitation light having the predetermined beam cross-section. The area of the predetermined beam cross-section of the excitation light is smaller than the area of the first light absorbing member and larger than the area of the second light absorbing member.

According to another aspect of the invention, there is provided an optical measurement method for irradiating a sample with excitation light and detecting measurement light. The optical measurement method includes: a step of irradiating a first light absorbing member, which is disposed in a light integrator, with the excitation light having a predetermined beam cross-section and detecting first measurement light, which is output from the light integrator, to acquire first corrective intensity data; a step of irradiating a second light absorbing member, which is disposed in the light integrator, with the excitation light having the predetermined beam cross-section and detecting second measurement light, which is output from the light integrator, to acquire second corrective intensity data; a step of irradiating the sample, which is disposed in the light integrator, with the excitation light having the predetermined beam cross-section and detecting measurement light, which is output from the light integrator, to acquire intensity data of the sample at one or a plurality of wavelengths; a step of calculating correction data based on the first corrective intensity data and the second corrective intensity data; and a step of calculating optical characteristics of the sample based on the intensity data of the sample and the correction data. The predetermined beam cross-section of the excitation light is covered with the first light absorbing member and covers the second light absorbing member.

Further, according to another aspect of the invention, there is provided an optical measurement method for irradiating a sample with excitation light and detecting measurement light. The optical measurement method includes: a step of irradiating a first light absorbing member, which is disposed in a light integrator, with the excitation light having a predetermined beam cross-section and detecting first measurement light, which is output from the light integrator, to acquire first corrective intensity data; a step of irradiating a second light absorbing member, which is disposed in the light integrator, with the excitation light having the predetermined beam cross-section and detecting second measurement light, which is output from the light integrator, to acquire second corrective intensity data; a step of irradiating the sample, which is disposed in the light integrator, with the excitation light having the predetermined beam cross-section and detecting measurement light that is output from the light integrator acquiring intensity data of the sample at one or a plurality of wavelengths; a step of calculating correction data based on the first corrective intensity data and the second corrective intensity data; and a step of calculating optical characteristics of the sample based on the intensity data of the sample and the correction data. The area of the predetermined beam cross-section of the excitation light is smaller than the area of the first light absorbing member and larger than the area of the second light absorbing member.

In the optical measurement device and the optical measurement method, the correction data is calculated based on the first corrective intensity data, which is detected when the first light absorbing member is irradiated with the excitation light having the predetermined beam cross-section covered with the first light absorbing member, and the second corrective intensity data that is detected when the second light absorbing member is irradiated with the excitation light having the predetermined beam cross-section covering the second light absorbing member. It is found that the correction data corresponds to the area ratio correction value. Accordingly, when the optical characteristics of the sample are calculated from the intensity data of the sample by using the correction data, optical characteristics can be accurately obtained even though the area of the beam cross-section of the excitation light is not measured actually and directly.

In the optical measurement device according to the aspect of the invention, the correction data may be a correction value that is calculated from a ratio of a first absorptance calculated based on the first corrective intensity data and a second absorptance calculated based on the second corrective intensity data. In the optical measurement method according to the aspect of the invention, the step of calculating the correction data can calculate the correction data from a ratio of a first absorptance calculated based on the first corrective intensity data and a second absorptance calculated based on the second corrective intensity data.

In the optical measurement device according to the aspect of the invention, the correction data may be a correction value that is calculated from a ratio of a first reflectance calculated based on the first corrective intensity data and a second reflectance calculated based on the second corrective intensity data. In the optical measurement method according to the invention, the step of calculating the correction data can calculate the correction data from a ratio of a first reflectance calculated based on the first corrective intensity data and a second reflectance calculated based on the second corrective intensity data.

In the optical measurement device and the optical measurement method according to the aspects of the invention, the correction data may be correction values at a plurality of wavelengths. In this case, for example, the correction data can be applied to a case in which optical characteristics are calculated from the intensity data of the sample at the plurality of wavelengths.

In the optical measurement device and the optical measurement method according to the aspects of the invention, as the specific structure, which is used to obtain the above-mentioned effects, the first light absorbing member and the second light absorbing member may be made of materials having the same absorptance.

In the optical measurement device according to the aspect of the invention, the area of the sample at an irradiation position of the excitation light may be equal to the area of the second light absorbing member at the irradiation position of the excitation light, the predetermined beam cross-section of the excitation light may cover the sample, and the optical characteristic calculation unit may be configured to calculate an absorptance or a reflectance of the sample as the optical characteristics based on the intensity data of the sample and the correction data. In the optical measurement method according to the aspect of the invention, the area of the sample at an irradiation position of the excitation light may be equal to the area of the second light absorbing member at the irradiation position of the excitation light, the predetermined beam cross-section of the excitation light may cover the sample, and the step of calculating the optical characteristics of the sample may calculate an absorptance or a reflectance of the sample as the optical characteristics based on the intensity data of the sample and the correction data.

In a case in which the predetermined beam cross-section of the excitation light covers the sample, an absorptance or a reflectance to be calculated tends to be estimated so as to be different from a true value. According to the aspect of the invention, when an absorptance or a reflectance of the sample is calculated from the intensity data of the sample by using the correction data, the absorptance or the reflectance can be accurately obtained even though the area of the beam cross-section of the excitation light is not directly measured.

In the optical measurement device according to the aspect of the invention, the area of the sample at an irradiation position of the excitation light may be equal to the area of the first light absorbing member at the irradiation position of the excitation light, the predetermined beam cross-section of the excitation light may be covered with the sample, and the optical characteristic calculation unit may be configured to calculate internal quantum efficiency of the sample as the optical characteristics based on the intensity data of the sample and the correction data. In the optical measurement method according to the aspect of the invention, the area of the sample at an irradiation position of the excitation light may be equal to the area of the first light absorbing member at the irradiation position of the excitation light, the predetermined beam cross-section of the excitation light may be covered with the sample; and the step of calculating the optical characteristics of the sample may calculate internal quantum efficiency of the sample as the optical characteristics based on the intensity data of the sample and the correction data.

In a case in which the predetermined beam cross-section of the excitation light is covered with the sample, internal quantum efficiency to be calculated tends to be estimated so as to be different from a true value. According to the aspect of the invention, when the internal quantum efficiency of the sample is calculated from the intensity data of the sample by using the correction data, the internal quantum efficiency can be accurately obtained even though the area of the beam cross-section of the excitation light is not directly measured.

In the optical measurement device according to the aspect of the invention, the predetermined beam cross-section, which is covered with the first light absorbing member, may have an area smaller than the area of the first light absorbing member at the irradiation position of the excitation light, and the predetermined beam cross-section, which covers the second light absorbing member, may have an area larger than the area of the second light absorbing member at the irradiation position of the excitation light. In the optical measurement method according to the aspect of the invention, the predetermined beam cross-section, which is covered with the first light absorbing member, may have an area smaller than the area of the first light absorbing member at the irradiation position of the excitation light, and the predetermined beam cross-section, which covers the second light absorbing member, may have an area larger than the area of the second light absorbing member at the irradiation position of the excitation light.

Advantageous Effects of Invention

According to the aspects of the invention, it is possible to provide an optical measurement device and an optical measurement method that can accurately obtain optical characteristics even though not directly measuring the area of a beam cross-section of excitation light.

BRIEF DESCRIPTION OF DRAWINGS

FIG. 4 is a diagram illustrating a sample holder of the optical measurement device of FIG. 1.

FIG. 8 is a flowchart illustrating an optical measurement method that is performed by the optical measurement device of FIG. 1.

DESCRIPTION OF EMBODIMENTS

Figure 1:
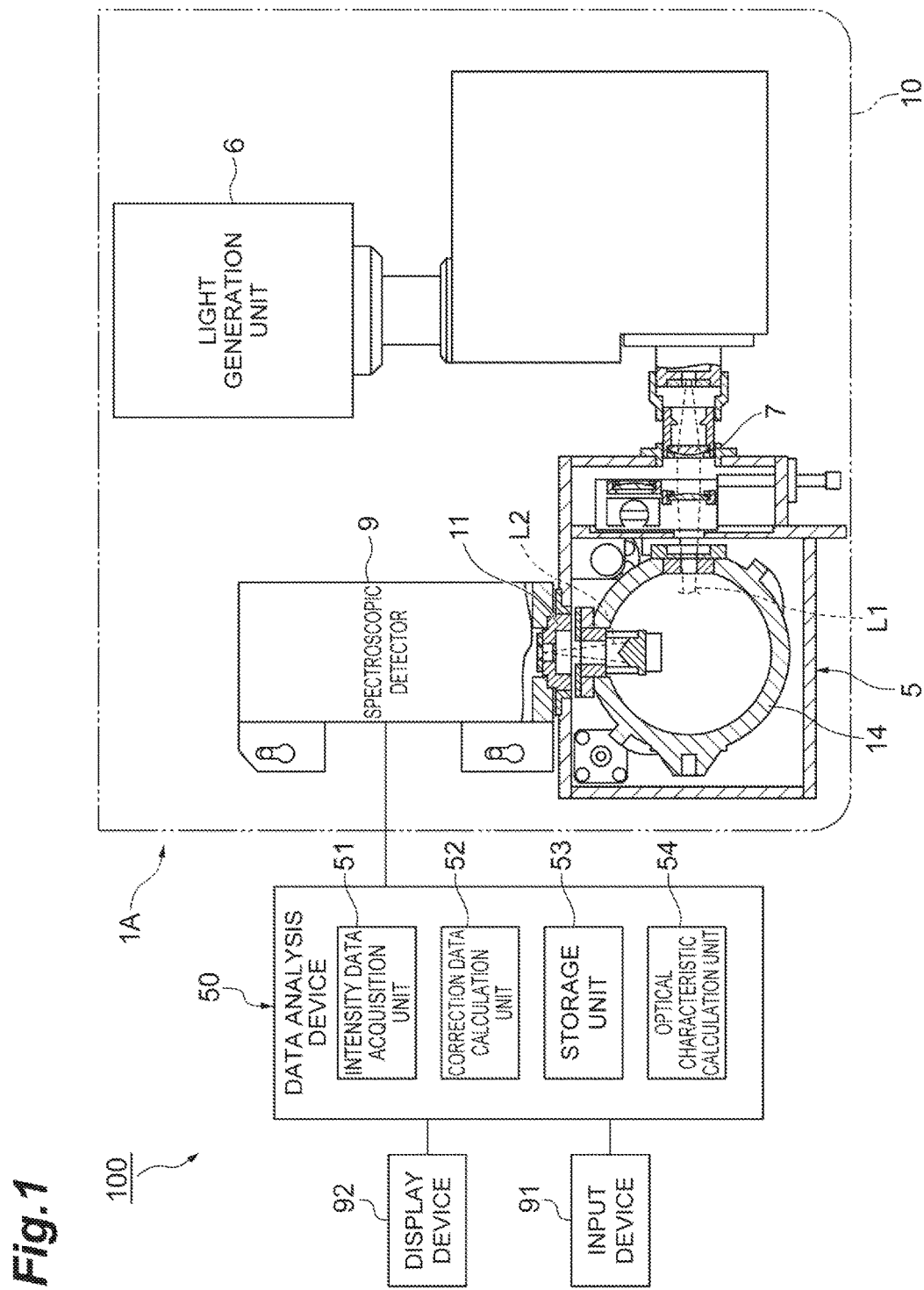
FIG. 1 is a diagram illustrating the configuration of an optical measurement device according to an embodiment.

Preferred embodiments of the invention will be described in detail below with reference to the drawings. Meanwhile, the same or corresponding elements in the following description are denoted by the same reference numerals and repeated description will be omitted.

FIG. 1 is a diagram illustrating the configuration of an optical measurement device according to an embodiment. As illustrated in FIG. 1, the optical measurement device 100 according to this embodiment measures or evaluates optical characteristics, such as fluorescence characteristics, of a sample as a sample, which is an object to be measured, by a photoluminescence method (PL method). The sample is, for example, a fluorescent sample, such as an organic EL (Electroluminescence) material or a luminescent material for a white LED (Light Emitting Diode), a FPD (Flat Panel Display), or the like. A material having the form of, for example, powder, liquid (solution), a solid, or a thin film can be used as the sample.

Examples of the optical characteristics include an absorptance, internal quantum efficiency (emission quantum yield), and external quantum efficiency. The absorptance is a parameter relating to the number of photons to be absorbed. The internal quantum efficiency is a parameter relating to a ratio of the number of photons of light, which is emitted due to luminescence, to the number of photons of light to be absorbed. The external quantum efficiency is a parameter relating to the number of photons to be emitted. The external quantum efficiency is the product of the absorptance and the internal quantum efficiency. An absorptance is contrary to a reflectance that is a parameter relating to the number of photons to be reflected. An absorptance has the same meaning as "1-reflectance".

The optical measurement device 100 includes a main body 1A, a data analysis device 50, an input device 91, and a display device 92. Meanwhile, in FIG. 1, the main body 1A is illustrated in a plan view of which a part is illustrated as a cross-section. In FIG. 1, for the sake of convenience, the cross-section of an integrating sphere 14 to be described below is illustrated as an end face (the same applies to FIGS. 2 and 3).

Figure 2:
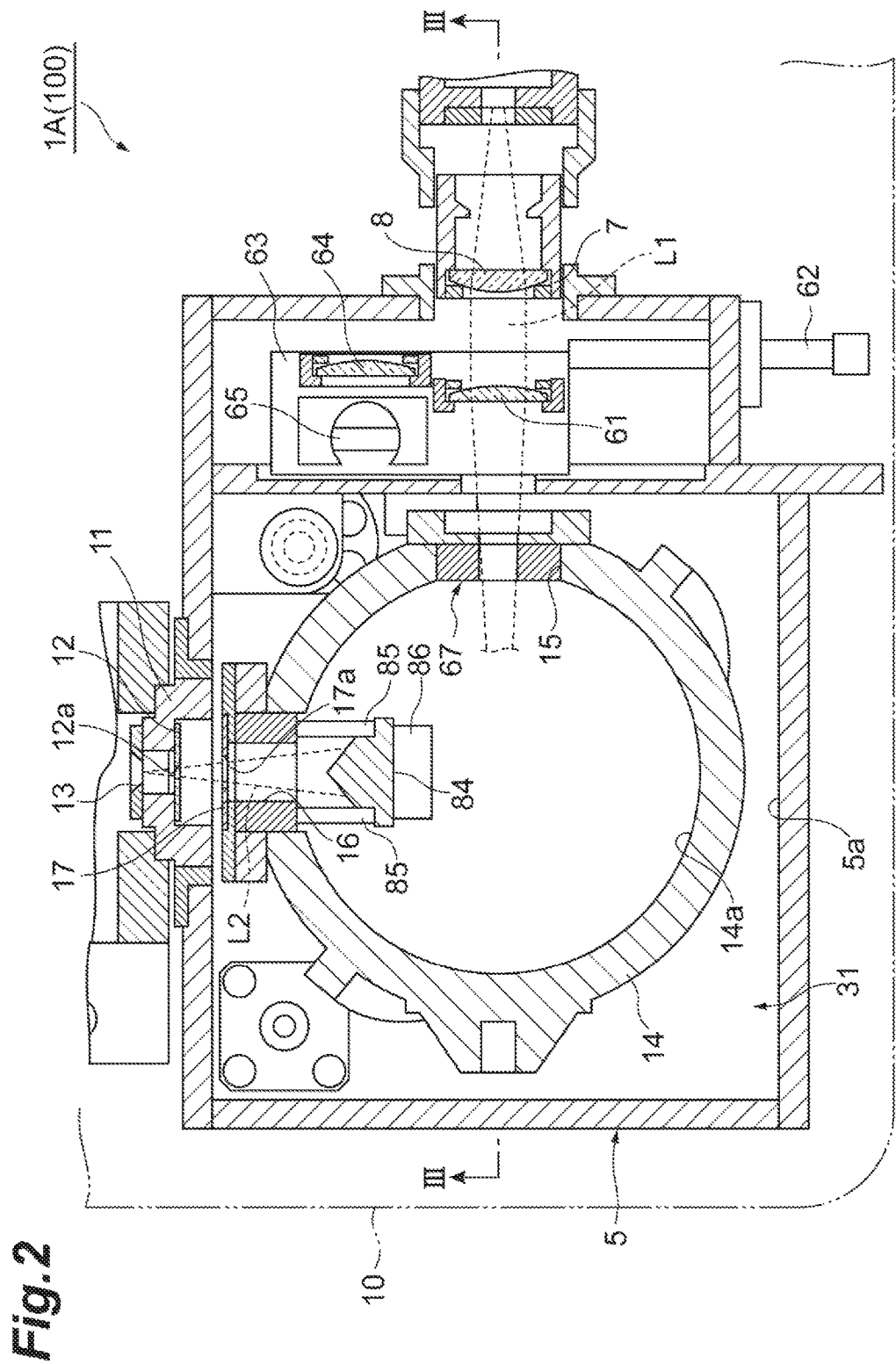
FIG. 2 is an enlarged view of the inside of a dark box of the optical measurement device of FIG. 1 and a peripheral portion thereof.
Figure 3:
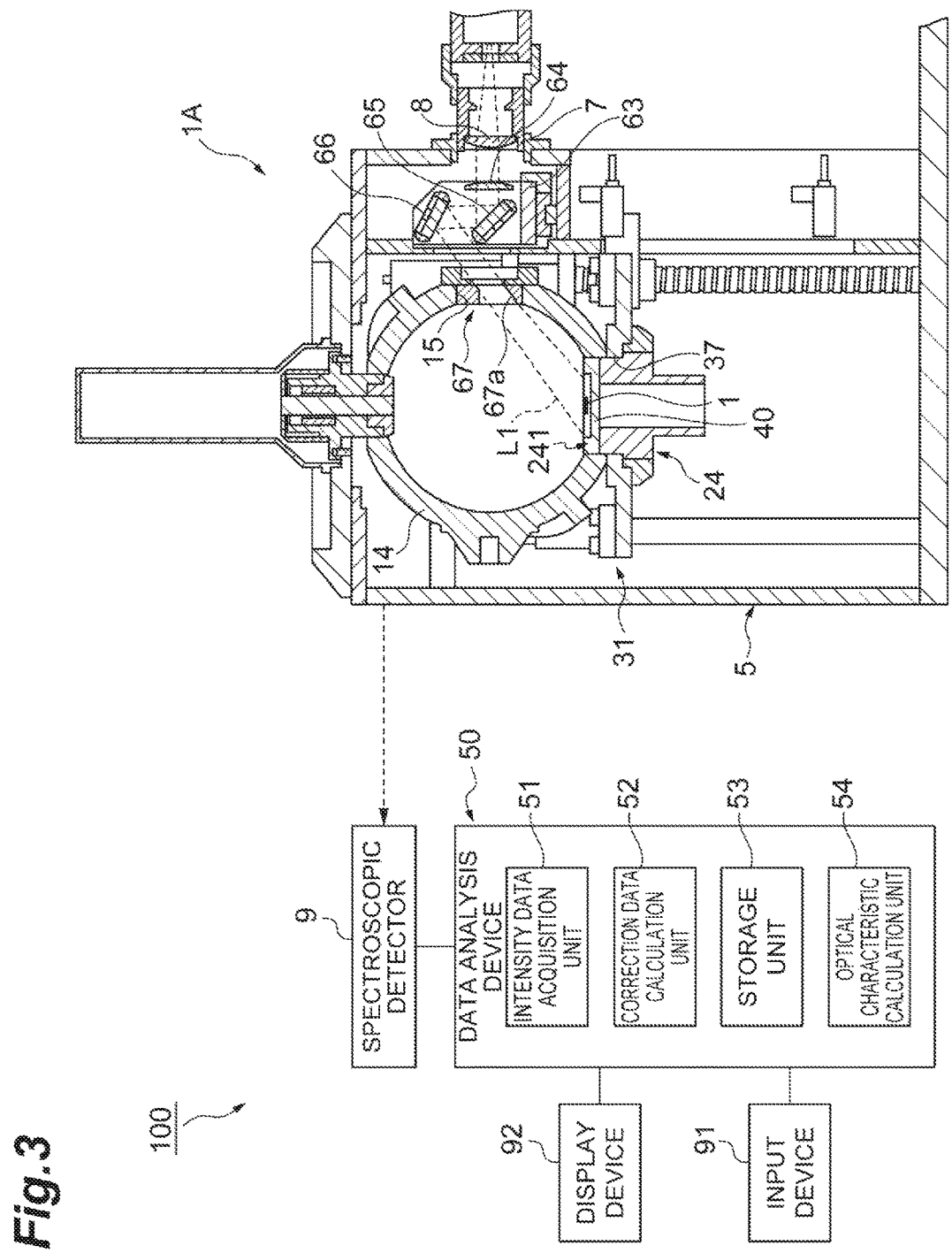
FIG. 3 is a diagram illustrating main parts of the optical measurement device of FIG. 1.

FIG. 2 is an enlarged view of the inside of a dark box of the optical measurement device of FIG. 1 and a peripheral portion thereof, and FIG. 3 is a diagram illustrating main parts of the optical measurement device of FIG. 1. The main body 1A of FIG. 3 is illustrated in a cross-sectional view taken along line III-III of FIG. 2. As illustrated in FIGS. 1 to 3, the main body 1A irradiates a sample 1 with excitation light L1 having a predetermined wavelength and detects measurement light L2 that is generated in response to the irradiation. The main body 1A includes a dark box 5.

The dark box 5 is a rectangular parallelepiped box body made of metal. The dark box 5 blocks light that enters from the outside. Coating, which uses a material absorbing the excitation light L1 and the measurement light L2, or the like is performed on an inner surface 5a of the dark box 5. A light output portion 7, which outputs the excitation light L1, of a light generation unit 6, is connected to one side wall of the dark box 5. The light generation unit 6 is an excitation light source that includes, for example, a xenon lamp, a spectrometer, and the like. The light generation unit 6 generates the excitation light L1. The excitation light L1 is collimated by a lens 8, which is provided in the light output portion 7, and is input to the dark box 5.

A light input portion 11 of a spectroscopic detector (photodetector) 9 is connected to the rear wall of the dark box 5. The spectroscopic detector 9 is optically connected to the integrating sphere 14. The measurement light L2 is reduced by an opening 12a of an aperture, which is a diaphragm member 12 provided in the light input portion 11, and is input to the spectroscopic detector 9 through a slit 13. The spectroscopic detector 9 decomposes the measurement light L2 into wavelength components, detects the wavelength components, and outputs the wavelength spectral data of the measurement light L2 to the data analysis device 50 as the intensity data of the sample 1 at a plurality of wavelengths.

The spectroscopic detector 9 outputs first and second corrective intensity data and first and second reference intensity data to the data analysis device 50 by detecting the measurement light as described below. A multi-channel detector formed of, for example, a spectrometer, a CCD sensor (or a CMOS sensor), or the like is used as the spectroscopic detector 9. Meanwhile, the intensity data at a plurality of wavelengths can be represented as, for example, data (spectroscopic data) where a horizontal axis represents a wavelength and a vertical axis represents intensity.

An integrating sphere (light integrator) 14 is disposed in the dark box 5. The integrating sphere 14 includes an inner surface 14a, which diffuses and reflects light input to the integrating sphere 14, therein. A high-diffusion reflective agent, such as barium sulfate, is applied to the inner surface 14a of the integrating sphere 14, or the inner surface 14a of the integrating sphere 14 is made of a high-reflective material, which has a reflectance close to 1, such as FIFE or Spectralon (registered trademark). A light input opening 15 through which the excitation light L1 is input and a light output opening 16 through which the measurement light L2 is output are formed in the integrating sphere 14. The dark box 5, the light generation unit 6, and the spectroscopic detector 9 are received in a housing 10 that is made of metal. Meanwhile, the optical axis of the excitation light L1, which is output from the light output portion 7 of the light generation unit 6, and the optical axis of the measurement light L2, which is input to the light input portion 11 of the spectroscopic detector 9, are substantially orthogonal to each other in a horizontal plane.

In the main body 1A, an opening 37 allowing a lower portion of the integrating sphere 14 and a stage 31, to which the integrating sphere 14 is fixed, to communicate with each other is formed at the lower portion of the integrating sphere 14 and the stage 31. A sample holder 24, which is detachably mounted from the lower side of the stage 31, is provided at the opening 37. That is, the sample holder 24 is detachably mounted on the integrating sphere 14. The sample holder 24 allows a sample container 40, which receives the sample 1, to be disposed at least in the integrating sphere 14.

The main body 1A includes a handle 62 as optical path switching means for switching the optical path of the excitation light L1. A stage 63 is moved in the main body 1A by the handle 62, so that a lens 61 and a collimator lens 64 are switched. During indirect excitation (in a state in which the sample 1 is not directly irradiated with the excitation light L1), the excitation light L1 is focused in the dark box 5 by the lens 61 and is input to the integrating sphere 14 through the light input opening 15 (see FIG. 2). During direct excitation (in a state in which the sample 1 is directly irradiated with the excitation light L1), the excitation light L1 is focused in the dark box 5 by the collimator lens 64, is sequentially reflected by mirrors 65 and 66, and is input to the integrating sphere 14 (see FIG. 3).

An aperture 67 is provided at the light input opening 15 of the integrating sphere 14. A notch 67a is formed on at least a part of the opening of the aperture 67. The shape of the notch 67a is formed so that the excitation light L1 emitted to the sample container 40, a first correction member 70, and a second correction member 80 has a predetermined beam cross-section (beam diameter). The collimator lens 64, the mirrors 65 and 66, and the aperture 67 form an optical system that irradiates the sample 1 with the excitation light L1. The optical system is optically connected to the integrating sphere 14. In the optical system, the excitation light L1, which is input to the dark box 5, is made parallel by the collimator lens 64, is sequentially reflected by the mirrors 65 and 66, passes through the aperture 67, and is input to the integrating sphere 14. Accordingly, the sample container 40 of the sample holder 24 is irradiated with the excitation light L1 having a predetermined beam cross-section D (see FIG. 5). Meanwhile, the optical system is not limited to the structure that includes the collimator lens 64, the mirrors 65 and 66, and the aperture 67, and can be formed in various forms. For example, the optical system may be formed of a light guide that optically connects the light generation unit 6 to the integrating sphere 14. The predetermined beam cross-section D of the excitation light L1 has a size of, for example, 4.8 mm×12 mm.

A diaphragm member 17 is provided at the light output opening 16 of the integrating sphere 14. Accordingly, the measurement light L2 is reduced by an opening 17a, which is an aperture of the diaphragm member 17, and is output to the outside of the integrating sphere 14. A baffle 84 is disposed in the integrating sphere 14 at a position facing the light output opening 16. The baffle 84 is supported by support columns 85 that stand on the inner surface 14a of the integrating sphere 14. A baffle 86 is integrally formed on the inner surface 14a of the integrating sphere 14. The baffles 84 and 86 prevent the measurement light L2 from being directly input to the light input portion 11 of the spectroscopic detector 9.

FIG. 4(A) is a plan view illustrating the sample holder of the optical measurement device of FIG. 1, and FIG. 4(B) is an end view taken along line IVb-IVb of FIG. 4(A). As illustrated in FIG. 4, the sample holder 24 allows the sample container 40, which receives the sample 1 and is to be described below, to be disposed in the integrating sphere 14 as an object to be irradiated. As described below, the sample holder 24 allows the first correction member 70, which can receive a first light absorbing member A, and the second correction member 80, which can receive a second light absorbing member B, to be disposed in the integrating sphere 14 as an object to be irradiated, instead of the sample container 40. The sample holder 24 includes a pedestal 241 on which an object to be irradiated is placed.

The pedestal 241 is made of a high-reflective material as in the case of the inner surface 14a of the integrating sphere 14. The pedestal 241 has, for example, a white color. The pedestal 241 is a portion, which is exposed to the integration space of the integrating sphere 14, of the sample holder 24. The pedestal 241 is formed in a circular external shape when seen from above. Holding portions 242 protrude from an upper portion of the outer peripheral portion of the pedestal 241. The holding portions 242 are provided with notches. An object to be irradiated is placed in the notches of the holding portions 242, so that the holding portions 242 hold the object to be irradiated.

Figure 5:
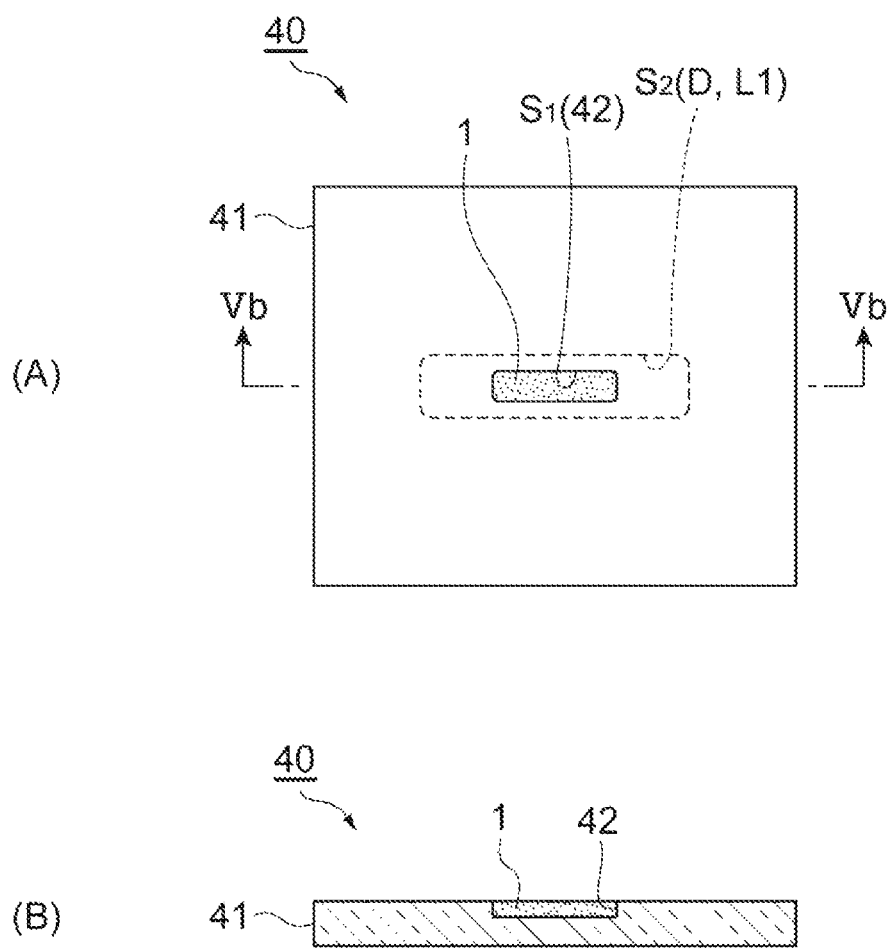
FIG. 5 is a diagram illustrating a sample container of the optical measurement device of FIG. 1.

FIG. 5(A) is a plan view illustrating the sample container 40 and FIG. 5(B) is a cross-sectional view taken along line Vb-Vb of FIG. 5(A). As illustrated in FIG. 5, the sample container 40 is a member where the sample 1 is disposed. The sample container 40 includes a substrate 41 for a sample that is formed in the shape of a rectangular plate. The substrate 41 for a sample is provided with a sample receiving portion 42. The sample receiving portion 42 is a recess that receives the sample 1. The sample container 40 is made of, for example, a transparent (light transmissive) material, such as quartz or synthetic quartz, in order to suppress that the sample container 40 absorbs light. Meanwhile, the sample container 40 may not be completely transparent. The substrate 41 for a sample may be formed in other shapes such as the shape of a circular plate.

The sample receiving portion 42 has a long shape when seen from above. The sample receiving portion 42 receives the sample 1 so that the sample 1 is surrounded by (that is, is covered with) the predetermined beam cross-section D of the excitation light L1 to be emitted. In other words, the sample receiving portion 42 receives the sample 1 so that the sample 1 is included (encompassed) in the predetermined beam cross-section D. That is, the predetermined beam cross-section D of the excitation light L1 at the position of the sample receiving portion 42 surrounds a portion of the sample 1 that is exposed from the sample receiving portion 42. Accordingly, a range of the sample container 40, which is irradiated with the excitation light L1, includes a range in which the sample 1 is disposed on the substrate 41 for a sample (exposed range). Meanwhile, the sample receiving portion 42 may have other shapes, such as a circular shape, when seen from above.

At an irradiation position where the sample 1 is irradiated with the excitation light L1, the area $S_2$ of the predetermined beam cross-section D is larger than the area $S_1$ of the sample 1 (the area of the sample 1 exposed from the sample receiving portion 42 in the sample container 40). In other words, when seen in the irradiation direction of the excitation light L1, the area $S_2$ of the predetermined beam cross-section D is larger than the area $S_1$ of the sample 1. For example, the predetermined beam cross-section D has a size of 4.8 mm×12 mm as described above, and a region corresponding to the area $S_1$ of the sample 1 has a size of 4 mm×10 mm.

FIG. 6(A) is a plan view illustrating the first correction member where the first light absorbing member is not received, FIG. 6(B) is a cross-sectional view taken along line VIb-VIb of FIG. 6(A), FIG. 6(C) is a plan view illustrating the first correction member where the first light absorbing member is received, and FIG. 6(D) is a cross-sectional view taken along line VId-VId of FIG. 6(C).

Figure 6:
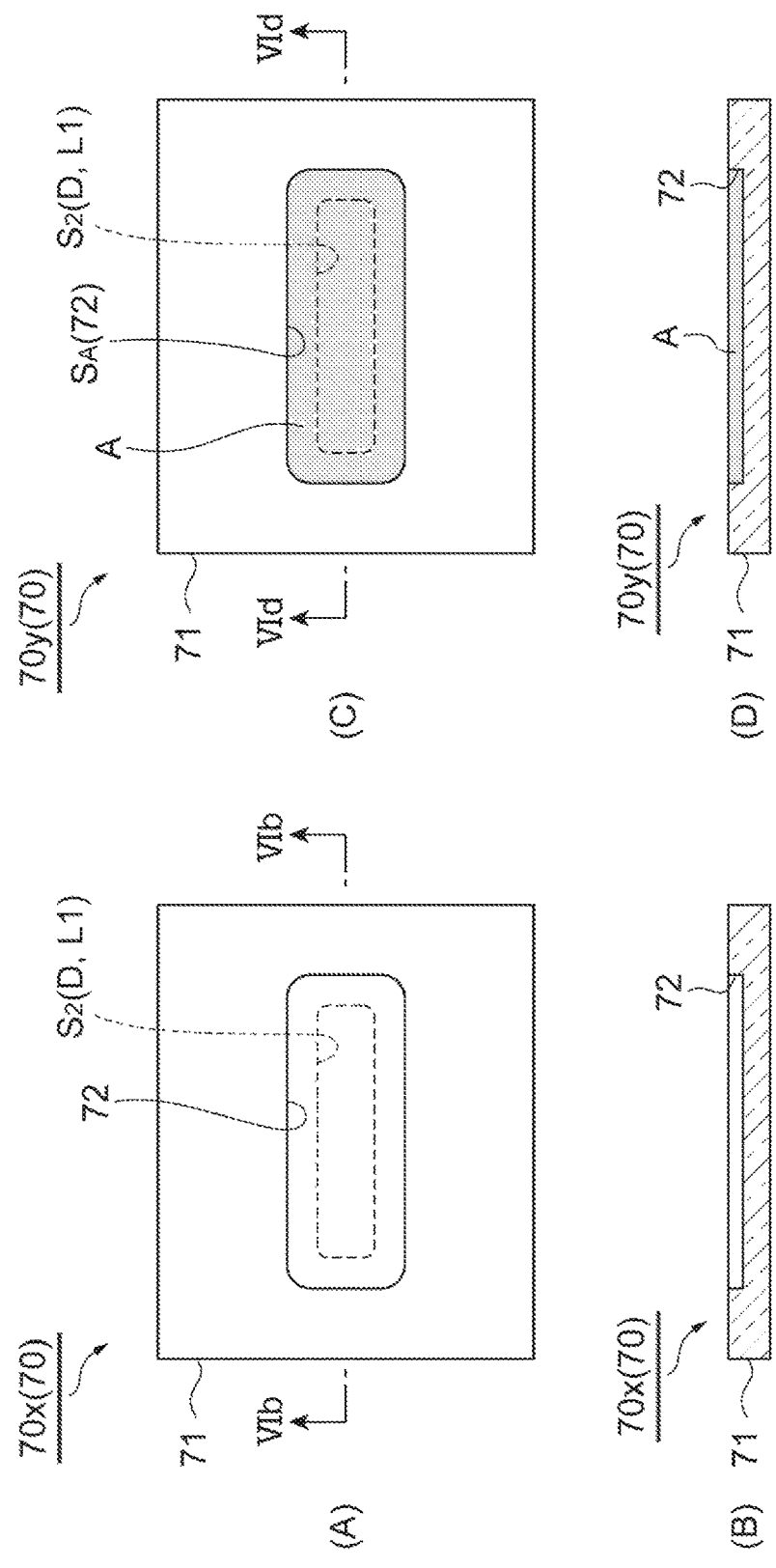
FIG. 6 is a diagram illustrating a first correction member of the optical measurement device of FIG. 1.

As illustrated in FIG. 6, the first correction member 70 is a member where the first light absorbing member A is disposed. The first correction member 70 includes a first substrate 71 for correction that has the shape of the same rectangular plate as the substrate 41 for a sample. The first correction member 70 is made of, for example, a transparent material, such as quartz or synthetic quartz, as in the case of the sample container 40. The first substrate 71 for correction is provided with a first receiving portion 72 for correction as a recess that receives the first light absorbing member A. The first light absorbing member A is made of a non-luminescent solid material having a high absorptance. Examples of the first light absorbing member A include a polyacetal resin (acetal resin) and a polyurethane resin. Here, the first light absorbing member A is filled in the entire first receiving portion 72 for correction so that the first receiving portion 72 for correction is completely closed.

The first receiving portion 72 for correction has a long shape when seen from above. Since the shape of the first receiving portion 72 for correction has a long axis, the area of the opening of the first receiving portion 72 for correction can be increased. The first receiving portion 72 for correction receives the first light absorbing member A so that the first light absorbing member A surrounds (that is, covers) the predetermined beam cross-section D of the excitation light L1 to be emitted. In other words, the first receiving portion 72 for correction receives the first light absorbing member A so that the first light absorbing member A includes (encompasses) the predetermined beam cross-section D. That is, the predetermined beam cross-section D of the excitation light L1 at the position of the first correction member 70 is surrounded by a portion of the first light absorbing member A that is exposed from the first receiving portion 72 for correction. Accordingly, a range of the first correction member 70, which is irradiated with the excitation light L1, is included in a range in which the first light absorbing member A is disposed on the first substrate 71 for correction (exposed range). Meanwhile, the first receiving portion 72 for correction may have other shapes, such as a circular shape, when seen from above.

At an irradiation position where the first light absorbing member A is irradiated with the excitation light L1, the area $S_2$ of the predetermined beam cross-section D is smaller than the area $S_A$ of the first light absorbing member A (the area of the first light absorbing member A exposed from the first receiving portion 72 for correction in the first correction member 70). In other words, when seen in the irradiation direction of the excitation light L1, the area $S_2$ of the predetermined beam cross-section D is smaller than the area $S_A$ of the first light absorbing member A. For example, the predetermined beam cross-section D has a size of 4.8 mm×12 mm as described above, and a region corresponding to the area $S_A$ of the first light absorbing member A has a size of 8 mm×20 mm.

FIG. 7(A) is a plan view illustrating the second correction member where the second light absorbing member is not received, FIG. 7(B) is a cross-sectional view taken along line VIIb-VIIb of FIG. 7(A), FIG. 7(C) is a plan view illustrating the second correction member where the second light absorbing member is received, and FIG. 7(D) is a cross-sectional view taken along line VIId-VIId of FIG. 7(C).

Figure 7:
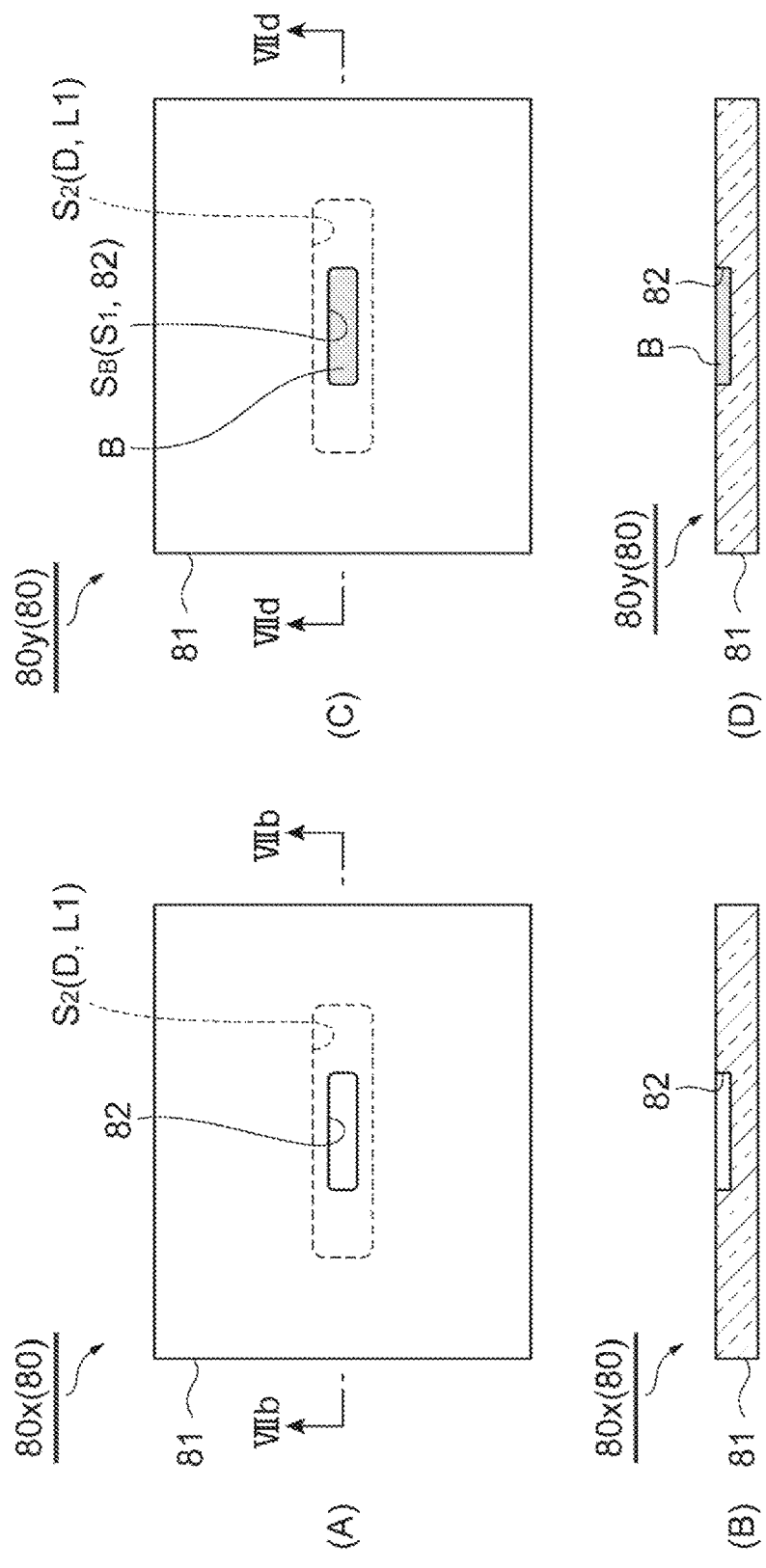
FIG. 7 is a diagram illustrating a second correction member of the optical measurement device of FIG. 1.

As illustrated in FIG. 7, the second correction member 80 is a member where the second light absorbing member B is disposed. The second correction member 80 has the same structure as the sample container 40 (see FIG. 5) except that the second light absorbing member B is received instead of the sample 1. That is, the second correction member 80 includes a second substrate 81 for correction having the shape of the same rectangular plate as the sample container 40, and is made of, for example, a transparent material, such as quartz or synthetic quartz. The second correction member 80 is provided with a second receiving portion 82 for correction, which has the same shape as the sample receiving portion 42, as a recess that receives the second light absorbing member B. The second light absorbing member B is made of a non-luminescent solid material having a high absorptance. The second light absorbing member B may be made of a material that has the same absorptance as the material of the first light absorbing member A. Here, the second light absorbing member B is filled in the entire second receiving portion 82 for correction so that the second receiving portion 82 for correction is completely closed.

When seen in a direction where the excitation light L1 is emitted, the second receiving portion 82 for correction receives the second light absorbing member B so that the second light absorbing member B is surrounded by (that is, is covered with) the predetermined beam cross-section D of the excitation light L1 to be emitted. In other words, the second receiving portion 82 for correction receives the second light absorbing member B so that the second light absorbing member B is included (encompassed) in the predetermined beam cross-section D. That is, the predetermined beam cross-section D of the excitation light L1 at the position of the second correction member 80 surrounds a portion of the second light absorbing member B that is exposed from the second receiving portion 82 for correction. Accordingly, a range of the second correction member 80, which is irradiated with the excitation light L1, includes a range in which the second light absorbing member B is disposed on the second substrate 81 for correction (exposed range). Meanwhile, the second receiving portion 82 for correction may have other shapes, such as a circular shape, when seen from above.

At an irradiation position where the second light absorbing member B is irradiated with the excitation light L1, the area $S_B$ of the second light absorbing member B (the area of the second light absorbing member B exposed from the second receiving portion 82 for correction in the second correction member 80) is substantially equal to the area $S_1$ of the sample 1 since the sample receiving portion 42 and the second receiving portion 82 for correction have the same shape. The area $S_2$ of the predetermined beam cross-section D is larger than the area $S_B$ of the second light absorbing member B. In other words, when seen in the irradiation direction of the excitation light L1, the area $S_2$ of the predetermined beam cross-section D is larger than the area $S_B$ of the second light absorbing member B. For example, the predetermined beam cross-section D has a size of 4.8 mm×12 mm as described above, and a region corresponding to the area $S_B$ of the second light absorbing member B has a size of 4 mm×10 mm.

Returning to FIGS. 1 and 3, the data analysis device 50 performs necessary data analysis on intensity data, which are output from the spectroscopic detector 9, and acquires information about the sample 1. The data analysis device 50 includes a processor and a memory (storage), and is, for example, a computer, such as a personal computer. The data analysis device 50 is electrically connected to the spectroscopic detector 9. The data analysis device 50 includes an intensity data acquisition unit 51 that acquires various kinds of intensity data at a plurality of wavelengths from the spectroscopic detector 9, a correction data calculation unit 52 that calculates correction data based on the intensity data acquired by the intensity data acquisition unit 51, a storage unit 53 that stores at least the correction data calculated by the correction data calculation unit 52, and an optical characteristic calculation unit 54 that calculates optical characteristics (spectroscopic characteristics) of the sample 1 based on the intensity data acquired by the intensity data acquisition unit 51 and the correction data stored in the storage unit 53. The intensity data acquisition unit 51, the correction data calculation unit 52, the storage unit 53, and the optical characteristic calculation unit 54 are electrically connected to each other. The storage unit 53 is formed of the memory of the data analysis device 50 and/or a storage, such as an external storage electrically connected to the data analysis device 50. The intensity data acquisition unit 51, the correction data calculation unit 52, and the optical characteristic calculation unit 54 are realized by the processor of the data analysis device 50. The detail of the processing of the data analysis device 50 will be described below.

The input device 91 is used for the input of an instruction about data analysis or the like, the input of an analysis condition, and the like. The input device 91 is connected to the data analysis device 50. The display device 92 is used for the display of obtained data analysis results, and the like. The display device 92 is connected to the data analysis device 50.

Next, an optical measurement method, which is performed by the optical measurement device 100, will be described with reference to a flowchart of FIG. 8.

Acquisition of First Reference Intensity Data (S1)

First, only the first substrate 71 for correction of the first correction member 70, that is, a first correction member 70x (see FIG. 6) where the first light absorbing member A is not held is placed on the sample holder 24, and the sample holder 24 is mounted on the integrating sphere 14. In this state, the excitation light L1 generated by the light generation unit 6 is input to the integrating sphere 14 and the first correction member 70x is irradiated with the excitation light L1 having the predetermined beam cross-section D.

Then, measurement light, which is output from the integrating sphere 14, is detected by the spectroscopic detector 9 and first reference intensity data, which are reference intensity data at a plurality of wavelengths, are output to the data analysis device 50. The data analysis device 50 acquires first reference intensity data by the intensity data acquisition unit 51 and stores the first reference intensity data in the storage unit 53.

Acquisition of First Corrective Intensity Data (S2)

Subsequently, a first correction member 70$y$ (see FIG. 6) where the first light absorbing member A is received and held is placed on the sample holder 24, and the sample holder 24 is mounted on the integrating sphere 14. In this state, the excitation light L1 generated by the light generation unit 6 is input to the integrating sphere 14 and the first correction member 70$y$ is irradiated with the excitation light L1 having the predetermined beam cross-section D. At this time, the first light absorbing member A is irradiated with the excitation light L1 so that the first light absorbing member A surrounds the predetermined beam cross-section D.

Then, measurement light, which is output from the integrating sphere 14, (first measurement light) is detected by the spectroscopic detector 9 and first corrective intensity data, which are the intensity data of the first light absorbing member A at a plurality of wavelengths, axe output to the data analysis device 50. The data analysis device 50 acquires first corrective intensity data by the intensity data acquisition unit 51 and stores the first corrective intensity data in the storage unit 53.

Acquisition of Second Reference Intensity Data (S3)

Subsequently, only the second substrate 81 for correction of the second correction member 80, that is, a second correction member 80$x$ (see FIG. 7) where the second light absorbing member B is not held is placed on the sample holder 24, and the sample holder 24 is mounted on the integrating sphere 14. In this state, the excitation light L1 generated by the light generation unit 6 is input to the integrating sphere 14 and the second correction member 80$x$ is irradiated with the excitation light L1 having the predetermined beam cross-section D.

Then, measurement light, which is output from the integrating sphere 14, is detected by the spectroscopic detector 9 and second reference intensity data, which are reference intensity data at a plurality of wavelengths, are output to the data analysis device 50. The data analysis device 50 acquires second reference intensity data by the intensity data acquisition unit 51 and stores the second reference intensity data in the storage unit 53.

Acquisition of Second Corrective Intensity Data (S4)

Subsequently, a second correction member 80$y$ (see FIG. 7) where the second light absorbing member B is received and held is placed on the sample holder 24, and the sample holder 24 is mounted on the integrating sphere 14. In this state, the excitation light L1 generated by the light generation unit 6 is input to the integrating sphere 14 and the second correction member 80$y$ is irradiated with the excitation light L1 having the predetermined beam cross-section D. At this time, the second light absorbing member B is irradiated with the excitation light L1 so that the second light absorbing member B is surrounded by the predetermined beam cross-section D.

Then, measurement light, which is output from the integrating sphere 14, (second measurement light) is detected by the spectroscopic detector 9 and second corrective intensity data, which are the intensity data of the second light absorbing member B at a plurality of wavelengths, are output to the data analysis device 50. The data analysis device 50 acquires second corrective intensity data by the intensity data acquisition unit 51 and stores the second corrective intensity data in the storage unit 53.

Calculation of Correction Data (S5)

Subsequently, correction data are calculated by the correction data calculation unit 52. Specifically, first absorptances are calculated based on the first reference intensity data acquired in Step S1 and the first corrective intensity data acquired in Step S2. The first absorptances are relative values of the first corrective intensity data with respect to the first reference intensity data. Here, the first absorptances are calculated based on the following Equation (ii).

$$Ar = 1 - Lb/La \qquad \text{(ii)}$$

Ar: first absorptance
La: first reference intensity data
Lb: first corrective intensity data Second absorptances are calculated based on the second reference intensity data acquired in Step S3 and the second corrective intensity data acquired in Step S4. The second absorptances are relative values of the second corrective intensity data with respect to the second reference intensity data. Here, the second absorptances are calculated based on the following Equation (iii).

$$Ar' = 1 - Lb'/La' \qquad \text{(iii)}$$

Ar': second absorptance
La': second reference intensity data
Lb': second corrective intensity data Then, correction data $\alpha$, which are ratios of the first absorptances Ar and the second absorptances Ar', are calculated based on the first absorptances Ar and the second absorptances Ar'. The correction data $\alpha$ are correction values at a plurality of wavelengths. The correction data $\alpha$ are calculated according to, for example, the following Equation (7). The first absorptances Ar, the second absorptances Ar', and the correction data $\alpha$ are calculated as values for every wavelength, and are stored in the storage unit 53.

Acquisition of Intensity Data of Sample (S6)

Subsequently, the sample container 40 (see FIG. 5) where the sample 1 is received and held is placed on the sample holder 24, and the sample holder 24 is mounted on the integrating sphere 14. In this state, the excitation light L1 generated by the light generation unit 6 is input to the integrating sphere 14 and the sample container 40 is irradiated with the excitation light L1 having the predetermined beam cross-section D. At this time, the sample 1 is irradiated with the excitation light L1 so that the sample 1 is surrounded by the predetermined beam cross-section D.

Then, measurement light L2, which is output from the integrating sphere 14, is detected by the spectroscopic detector 9 and intensity data of the sample 1 at a plurality of wavelengths are output to the data analysis device 50. The data analysis device 50 acquires intensity data of the sample 1 by the intensity data acquisition unit 51 and stores the intensity data of the sample 1 in the storage unit 53.

Calculation of Optical Characteristics of Sample (S7)

Finally, the absorptances of the sample 1 are calculated by the optical characteristic calculation unit 54 based on the second reference intensity data acquired in Step S3, the intensity data of the sample 1 acquired in Step S6, and the correction data α calculated in Step S5. For example, the optical characteristic calculation unit 54 calculates the true absorptances Q of the sample 1 according to the following Equation (iv). Meanwhile, since the substrate 41 for a sample is the same as the second substrate 81 for correction, the second reference intensity data are used as the reference intensity data of the sample container 40 here.

$$Q=(1-Lb'/Lc) \times \alpha \qquad (iv)$$

The internal quantum efficiency (emission quantum yield) of the sample 1 is calculated by the optical characteristic calculation unit 54 based on the second reference intensity data acquired in Step S3 and the intensity data of the sample 1 acquired in Step S6. A publicly known calculation method can be used for the calculation of the internal quantum efficiency. Then, the optical characteristic calculation unit 54 calculates external quantum efficiency by the product of the calculated internal quantum efficiency and the absorptance.

Incidentally, it is found that optical characteristics can be accurately obtained using an area ratio correction value relating to a ratio of the area of the beam cross-section D of the excitation light L1 and the area of the sample 1. However, it is not easy to measure the area $S_2$ of the beam cross-section D in the integrating sphere 14. Further, for example, when intensity data at a plurality of wavelengths are to be detected, the size of the beam cross-section D varies according to wavelengths since the characteristics of an optical element depends on wavelengths. For this reason, since it is necessary to measure the area $S_2$ of the beam cross-section D for each wavelength in order to calculate the area ratio correction values for every wavelength, this is not realistic.

In this regard, in this embodiment, the correction data α are calculated based on the first corrective intensity data, which is obtained when the first light absorbing member A is irradiated with the excitation light L1 having the predetermined beam cross-section D surrounded by the first light absorbing member A, and the second corrective intensity data that is obtained when the second light absorbing member B is irradiated with the excitation light L1 having the predetermined beam cross-section D surrounding the second light absorbing member B; and the correction data α are stored in the storage unit 53. Then, optical characteristics are calculated using the correction data α. Accordingly, since it is found that the correction data α corresponds to the area ratio correction value as described in detail below, optical characteristics can be accurately obtained even though the area $S_2$ of the beam cross-section D of the excitation light L1 is not measured actually and directly.

That is, generally, the existing measurement of a reflectance and an absorptance is premised on conditions where the area $S_1$ of an object to be irradiated is larger than the area $S_2$ of the predetermined beam cross-section D of the excitation light L1 and the predetermined beam cross-section D is covered with the object to be irradiated. In this case, the following Equation (1) relating to a relative reflectance Ra' and the following Equation (2) relating to a first absorptance Ar (Ar=1−relative reflectance Ra'), which is a relative absorptance, are obtained. In the following description, an absolute reflectance Rr of a reference and an absolute reflectance Ra of an object to be irradiated are measurable physical quantities unique to a material. Other factors except for the area $S_1$ of the object to be irradiated are formed of functions of a wavelength (the same applies to the following description)

$$Ra'=Ra/Rr \qquad (1)$$

$$Ar=1-Ra/Rr \qquad (2)$$

On the other hand, an area weighted average reflectance represented in the following Equation (3) is defined using absolute reflectances Rr and Ra under conditions where the area $S_1$ of an object to be irradiated is smaller than the area $S_2$ of the predetermined beam cross-section D and the predetermined beam cross-section D surrounds the object to be irradiated. As in the cases of the above-mentioned Equations (1) and (2), the following Equation (4) relating to a relative reflectance Rgw' and the following Equation (5) relating to a second absorptance Ar' (Ar'=1−relative reflectance Rgw'), which is a relative absorptance, are obtained under a condition where the predetermined beam cross-section D surrounds the object to be irradiated.

$$Rwg=(S_1/S_2) \times Ra+((S_2-S_1)/S_2) \times Rr \qquad (3)$$

$$Rwg'=Rwg/Rr \qquad (4)$$

$$Ar'=1-Rwg/Rr \qquad (5)$$

The following Equation (3A) is obtained from the modification of the above-mentioned Equation (3). When the following Equation (3A) is arranged using the above-mentioned Equations (2) and (5), the following Equation (6) is derived. As a result, the following Equation (7) relating to the area ratio correction value $S_2/S_1$ is ultimately derived. Accordingly, the area ratio correction value $S_2/S_1$ is obtained from the first and second absorptances Ar and Ar'. As a result, the correction data α corresponds to the area ratio correction value $S_2/S_1$.

$$Rwg/Rr=(S_1/S_2) \times Ra/Rr+(S_2-S_1)/S_2$$

$$Rwg/Rr=(S_1/S_2) \times Ra/Rr+1-S_1/S_2$$

$$1-Rwg/Rr=(S_1/S_2) \times (1-Ra/Rr) \qquad (3A)$$

$$Ar'=(S_1/S_2) \times Ar$$

$$Ar=(S_2/S_1) \times Ar' \qquad (6)$$

$$S_2/S_1=Ar/Ar'=\alpha \qquad (7)$$

In this embodiment, the correction data α are correction values at a plurality of wavelengths. Accordingly, correction data α can be suitably applied to this embodiment that calculates optical characteristics from the intensity data of the sample 1 at a plurality of wavelengths.

Generally, an absorptance to be calculated tends to be estimated so as to be different from a true value in a case in which the predetermined beam cross-section D of the excitation light L1 covers the sample 1 (see Step S6). In contrast, since the correction data α are used in this embodiment, the absorptance Q of the sample 1 can be accurately calculated from the intensity data of the sample 1 even though the area $S_2$ of the beam cross-section D of the excitation light L1 is not directly measured. Accordingly, more accurate external quantum efficiency can be measured.

In addition, since both internal quantum efficiency and an absorptance can be measured in this embodiment, each of the internal quantum efficiency and the absorptance does not need to be measured by a separate device. Accordingly, when internal quantum efficiency and an absorptance are measured, device cost and complication can be suppressed and the amount of the sample 1 required for measurement can be reduced.

The preferred embodiments have been described above. However, the invention is not limited to the embodiments, and may be modified with departing from the scope described in each claim or may be applied to others.

The integrating sphere 14 has been used as the light integrator in the embodiments, but the light integrator may be an optical component that includes a surface diffusing and reflecting light therein and spatially integrates light therein. For example, an integrating hemisphere disclosed in Japanese Unexamined Patent Publication No. 2009-103654 may be used as the light integrator. In the embodiments, intensity data (spectroscopic data) at a plurality of wavelengths have been acquired and correction data α have been calculated as correction values at a plurality of wavelengths. However, intensity data at one wavelength may be acquired and correction data may be calculated as a correction value at one wavelength.

In the embodiments, the internal quantum efficiency of the sample 1 may be calculated based on the intensity data of the sample 1 and the correction data α. Specifically, the sample container 40 is formed to have the same structure as the first correction member 70, and the area $S_1$ of the sample 1 is made equal to the area $S_A$ of the first light absorbing member A so that the predetermined beam cross-section D is surrounded by the sample 1. Then, the internal quantum efficiency of the sample 1 may be calculated by the optical characteristic calculation unit 54 based on the first reference intensity data acquired in Step S1, the intensity data of the sample 1 acquired in Step S6, and the correction data α calculated in Step S5.

Since a self-absorption effect is improved by multiple scattering in a case in which the predetermined beam cross-section D of the excitation light L1 is covered with the sample 1, internal quantum efficiency to be calculated tends to be estimated so as to be different from a true value. Accordingly, when the internal quantum efficiency of the sample 1 is calculated using the correction data α (internal quantum efficiency is corrected using the correction data α), internal quantum efficiency can be accurately obtained even though the area $S_2$ of the beam cross-section D of the excitation light L1 is not directly measured.

In the embodiments, the first and second light absorbing members A and B have only to be materials that are different from the respective base materials (the first and second substrates 71 and 81 for correction) of the first and second correction members 70 and 80 and absorb light as much as possible. The first and second light absorbing members A and B are not particularly limited as long as the first and second light absorbing members A and B do not emit light. For example, when a material having a high absorptance is used for the first and second light absorbing members A and B, appropriate correction data α can be easily calculated.

In the embodiments, absorptances have been calculated based on the intensity data of the sample 1 and the correction data α. However, since an absorptance is a parameter that is contrary to a reflectance and has the same meaning as "1-reflectance", reflectances may be calculated based on the intensity data of the sample 1 and the correction data α. Likewise, the correction data may be a correction value that is calculated from a ratio of a first reflectance calculated based on the first corrective intensity data and a second reflectance calculated based on the second corrective intensity data.

In the embodiments, the first and second light absorbing members A and B have been received in the first and second receiving portions 72 and 82 for correction that are provided on the first and second correction members 70 and 80, respectively. However, the first and second receiving portions 72 and 82 for correction may not be provided, and the first and second light absorbing members A and B may be placed on the first and second substrates 71 and 81 for correction, respectively. Words of "the same" and "equal" include, for example, words of "approximately the same" and "approximately equal", respectively, and mean "substantially the same" and "substantially equal", respectively.

In a case in which the first and second substrates 71 and 81 for correction have the same shape in the embodiments (for example, in a case in which at least any of the opening areas, volumes, and depths of the first and second receiving portions 72 and 82 for correction are equal to each other), Step S3 is not performed and the first reference intensity data acquired in Step S1 may be used as the second reference intensity data.

Steps S1, S2, S3, S4, and S6 have been performed in this order in the embodiments, but these steps may be performed in any order (in a random order). When Step S5 is performed after Steps S1 to S4 before Step S7, Step S5 may be performed in parallel with, for example, Step S6. Steps S1 to S5 do not necessarily need to be performed whenever the optical characteristics of the sample 1 are measured. For example, Steps S1 to S5 may be performed at the time of factory shipment of the optical measurement device 100 so that correction data α are acquired, and the correction data α may be stored in the storage unit 53 in advance. Further, Steps S1 to S5 may be performed during correction after the elapse of a certain period of time.

In the embodiments, the area $S_2$ of the predetermined beam cross-section D has only to be set to be larger than the area $S_1$ of the sample 1 and the predetermined beam cross-section D has only to be adapted to surround (cover) the sample 1. Furthermore, the area $S_2$ of the predetermined beam cross-section D has only to be set to be smaller than the area $S_A$ of the first light absorbing member A and the predetermined beam cross-section D has only to be adapted to be surrounded (covered) with the sample 1. In addition, the area $S_2$ of the predetermined beam cross-section D has only to be set to be larger than the area $S_B$ of the second light absorbing member B and the predetermined beam cross-section D has only to be adapted to surround the sample 1. This structure can be realized by the adjustment of, for example, at least any of the optical system of the excitation light L1 and the shapes of the openings of the receiving portions 42, 72, and 82.

INDUSTRIAL APPLICABILITY

According to an aspect of the invention, an object of the invention is to provide an optical measurement device and an optical measurement method that can accurately obtain optical characteristics even though not directly measuring the area of the beam cross-section of excitation light.

REFERENCE SIGNS LIST

1: sample
9: spectroscopic detector (photodetector)
14: integrating sphere (light integrator)
53: storage unit
54: optical characteristic calculation unit
64: collimator lens (optical system)

65, 66: mirror (optical system)
67: aperture (optical system)
100: optical measurement device
A: first light absorbing member
B: second light absorbing member
D: predetermined beam cross-section
L1: excitation light
L2: measurement light

The invention claimed is:

1. An optical measurement device for irradiating a sample with excitation light and detecting measurement light, the optical measurement device comprising:
a light integrator in which the sample is disposed;
an optical system configured to irradiate the sample in the light integrator with the excitation light having a predetermined beam cross-section;
a photodetector configured to detect measurement light output from the light integrator and output intensity data at one or a plurality of wavelengths;
a storage in which correction data is stored; and
a computer electrically connected to the photodetector and the storage and configured to calculate optical characteristics of the sample based on the intensity data and the correction data,
wherein the correction data is a correction value calculated based on first corrective intensity data, which is a detection value of first measurement light output from the light integrator when a first light absorbing member disposed in the light integrator is irradiated with the excitation light having the predetermined beam cross-section, and second corrective intensity data, which is a detection value of second measurement light output from the light integrator when a second light absorbing member disposed in the light integrator is irradiated with the excitation light having the predetermined beam cross-section, and
the predetermined beam cross-section of the excitation light is covered with the first light absorbing member and covers the second light absorbing member.

2. The optical measurement device according to claim 1, wherein the correction data is a correction value that is calculated from a ratio of a first absorptance calculated based on the first corrective intensity data and a second absorptance calculated based on the second corrective intensity data.

3. The optical measurement device according to claim 1, wherein the correction data is a correction value that is calculated from a ratio of a first reflectance calculated based on the first corrective intensity data and a second reflectance calculated based on the second corrective intensity data.

4. The optical measurement device according to claim 1, wherein the correction data are correction values at a plurality of wavelengths.

5. The optical measurement device according to claim 1, wherein the first light absorbing member and the second light absorbing member are materials having the same absorptance.

6. The optical measurement device according to claim 1, wherein the area of the sample at an irradiation position of the excitation light is equal to the area of the second light absorbing member at the irradiation position of the excitation light,
the predetermined beam cross-section of the excitation light covers the sample, and
the computer is configured to calculate an absorptance or a reflectance of the sample as the optical characteristics based on the intensity data and the correction data.

7. The optical measurement device according to claim 1, wherein the area of the sample at an irradiation position of the excitation light is equal to the area of the first light absorbing member at the irradiation position of the excitation light,
the predetermined beam cross-section of the excitation light is covered with the sample, and
the computer is configured to calculate internal quantum efficiency of the sample as the optical characteristics based on the intensity data and the correction data.

8. The optical measurement device according to claim 1, wherein the predetermined beam cross-section, which is covered with the first light absorbing member, has an area smaller than the area of the first light absorbing member at the irradiation position of the excitation light, and
the predetermined beam cross-section, which covers the second light absorbing member, has an area larger than the area of the second light absorbing member at the irradiation position of the excitation light.

9. The optical measurement device according to claim 1, wherein the light integrator is an integrating sphere or an integrating hemisphere.

10. An optical measurement method for irradiating a sample with excitation light and detecting measurement light, the optical measurement method comprising:
irradiating a first light absorbing member, which is disposed in a light integrator, with the excitation light having a predetermined beam cross-section and detecting first measurement light, which is output from the light integrator, to acquire first corrective intensity data;
irradiating a second light absorbing member, which is disposed in the light integrator, with the excitation light having the predetermined beam cross-section and detecting second measurement light, which is output from the light integrator, to acquire second corrective intensity data;
irradiating the sample, which is disposed in the light integrator, with the excitation light having the predetermined beam cross-section and detecting measurement light, which is output from the light integrator, to acquire intensity data at one or a plurality of wavelengths;
calculating correction data based on the first corrective intensity data and the second corrective intensity data; and
calculating optical characteristics of the sample based on the intensity data and the correction data,
wherein the predetermined beam cross-section of the excitation light is covered with the first light absorbing member and covers the second light absorbing member.

11. The optical measurement method according to claim 10, wherein the light integrator is an integrating sphere or an integrating hemisphere.

12. The optical measurement method according to claim 10, wherein the calculating the correction data calculates the correction data based on a ratio of a first absorptance calculated based on the first corrective intensity data and a second absorptance calculated based on the second corrective intensity data.

13. The optical measurement method according to claim 10,
wherein the calculating the correction data calculates the correction data based on a ratio of a first reflectance calculated based on the first corrective intensity data and a second reflectance calculated based on the second corrective intensity data.

14. The optical measurement method according to claim 10,
wherein the correction data are correction values at a plurality of wavelengths.

15. The optical measurement method according to claim 10,
wherein the first light absorbing member and the second light absorbing member are materials having the same absorptance.

16. The optical measurement method according to claim 10,
wherein the area of the sample at an irradiation position of the excitation light is equal to the area of the second light absorbing member at the irradiation position of the excitation light,
the predetermined beam cross-section of the excitation light covers the sample, and
the calculating the optical characteristics of the sample calculates an absorptance or a reflectance of the sample is calculated as the optical characteristics based on the intensity data and the correction data.

17. The optical measurement method according to claim 10,
wherein the area of the sample at an irradiation position of the excitation light is equal to the area of the first light absorbing member at the irradiation position of the excitation light,
the predetermined beam cross-section of the excitation light is covered with the sample, and
the calculating the optical characteristics of the sample calculates internal quantum efficiency of the sample is calculated as the optical characteristics based on the intensity data and the correction data.

18. The optical measurement method according to claim 10,
wherein the predetermined beam cross-section, which is covered with the first light absorbing member, has an area smaller than the area of the first light absorbing member at the irradiation position of the excitation light, and
the predetermined beam cross-section, which covers the second light absorbing member, has an area larger than the area of the second light absorbing member at the irradiation position of the excitation light.

19. An optical measurement device for irradiating a sample with excitation light and detecting measurement light, the optical measurement device comprising:
a light integrator in which the sample is disposed;
an optical system configured to irradiate the sample in the light integrator with the excitation light having a predetermined beam cross-section;
a photodetector configured to detect measurement light output from the light integrator and output intensity data at one or a plurality of wavelengths;
a storage in which correction data is stored; and
a computer configured to calculate optical characteristics of the sample based on the intensity data and the correction data,
wherein the correction data is a correction value calculated based on first corrective intensity data, which is a detection value of first measurement light output from the light integrator when a first light absorbing member disposed in the light integrator is irradiated with the excitation light having the predetermined beam cross-section, and second corrective intensity data, which is a detection value of second measurement light output from the light integrator when a second light absorbing member disposed in the light integrator is irradiated with the excitation light having the predetermined beam cross-section, and
the area of the predetermined beam cross-section of the excitation light is smaller than the area of the first light absorbing member and larger than the area of the second light absorbing member.

20. An optical measurement method for irradiating a sample with excitation light and detecting measurement light, the optical measurement method comprising:
irradiating a first light absorbing member, which is disposed in a light integrator, with the excitation light having a predetermined beam cross-section and detecting first measurement light, which is output from the light integrator, to acquire first corrective intensity data;
irradiating a second light absorbing member, which is disposed in the light integrator, with the excitation light having the predetermined beam cross-section and detecting second measurement light, which is output from the light integrator, to acquire second corrective intensity data;
irradiating the sample, which is disposed in the light integrator, with the excitation light having the predetermined beam cross-section and detecting measurement light that is output from the light integrator acquiring intensity data at one or a plurality of wavelengths;
calculating correction data based on the first corrective intensity data and the second corrective intensity data; and
calculating optical characteristics of the sample based on the intensity data and the correction data,
wherein the area of the predetermined beam cross-section of the excitation light is smaller than the area of the first light absorbing member and larger than the area of the second light absorbing member.

* * * * *